(12) United States Patent
Fujisawa et al.

(10) Patent No.: US 6,262,330 B1
(45) Date of Patent: Jul. 17, 2001

(54) PRESSURE SENSITIVE ADHESIVE TAPE FOR SKIN AND BASE MATERIAL THEREFOR

(75) Inventors: Hiromichi Fujisawa; Fumio Tokumura, both of Tokyo (JP)

(73) Assignee: Nichiban Co., Ltd., Tokyo (JP)

( * ) Notice: Subject to any disclaimer, the term of this patent is extended or adjusted under 35 U.S.C. 154(b) by 0 days.

(21) Appl. No.: 09/601,429

(22) PCT Filed: Dec. 2, 1999

(86) PCT No.: PCT/JP99/06773

§ 371 Date: Aug. 1, 2000

§ 102(e) Date: Aug. 1, 2000

(87) PCT Pub. No.: WO00/32144

PCT Pub. Date: Jun. 8, 2000

(30) Foreign Application Priority Data

Dec. 2, 1998 (JP) .................................. 10-342824
Dec. 10, 1998 (JP) .................................. 10-351558

(51) Int. Cl.[7] .................................................. A61F 13/00
(52) U.S. Cl. ............................. 602/54; 602/41; 602/42; 602/43; 602/44; 602/45; 602/46
(58) Field of Search .................... 602/54, 41–47

(56) References Cited

FOREIGN PATENT DOCUMENTS

| | | |
|---|---|---|
| 0628320 | 5/1994 | (EP) . |
| 0779064 | 11/1996 | (EP) . |
| 5-65224 | 9/1991 | (JP) . |
| 5-131022 | 11/1991 | (JP) . |
| 6-16541 | 1/1992 | (JP) . |
| 5-279251 | 3/1992 | (JP) . |
| 9-154933 | 6/1992 | (JP) . |
| 6-13821 | 7/1992 | (JP) . |
| 7-157423 | 6/1993 | (JP) . |
| 7-138152 | 11/1993 | (JP) . |
| 7-206710 | 1/1994 | (JP) . |
| 8-117268 | 10/1994 | (JP) . |
| 6-343685 | 12/1994 | (JP) . |
| 2-1284 | 1/1998 | (JP) . |
| 7-275340 | 7/1998 | (JP) . |

Primary Examiner—Michael A. Brown
Assistant Examiner—Lolita M. Hamilton
(74) Attorney, Agent, or Firm—Dinsmore & Shohl LLP

(57) ABSTRACT

A pressure sensitive adhesive tape for skin, including a stretchable base material having good moisture permeability and a pressure sensitive adhesive layer formed on at least one side of the base material, wherein the adhesive tape has features that (a) the conformability to a stretchable film is at most 4.2 times as much as the stress of the stretchable film at 15% elongation, (b) the water-vapor transmission rate is at least 500 $g/m^2 \cdot 24$ h, and (c) the adhesive strength to bakelite is at most 1.5 N/15 mm, and a base material of a pressure sensitive adhesive tape for skin, including a microporous film formed from a resin composition containing a polyolefin resin and an inorganic filler, and having features that (1) the thickness is 40 to 200 $\mu$m, (2) the average pore size is 0.02 to 10 $\mu$m, (3) the air permeability is 10 to 400 sec/100 cc, (4) the water-vapor transmission rate is 1,000 to 20,000 $g/m^2 \cdot 24$ h, and (5) the stresses at 15% elongation in the machine direction and transverse direction is both 0.5 to 15 N/15 mm.

15 Claims, 2 Drawing Sheets

PRESSURE SENSITIVE ADHESIVE TAPE FOR SKIN AND BASE MATERIAL THEREFOR

TECHNICAL FIELD

The present invention relates to a pressure sensitive adhesive tape for skin, and more particularly a pressure sensitive adhesive tape for skin, which has stable tackiness upon sweating or during sticking for a long period of time and scarcely causes pain, corneum separation and skin irritation upon its peeling. The present invention also relates to a low-irritative pressure sensitive adhesive tape for skin, which has excellent conformability to skin and moisture permeability and stable adhesive strength and is lightened in pain, corneum separation and skin irritation upon its peeling. The present invention further relates to a base material suitable for use in such a low-irritative pressure sensitive adhesive tape for skin. The pressure sensitive adhesive tapes for skin according to the present invention are particularly suitable for use as medical pressure sensitive adhesive tapes for protection of the affected skin parts and operated sites, percutaneous absorption of drugs, etc.

BACKGROUND ART

Various kinds of pressure sensitive adhesive tapes for skin have heretofore been developed for protection of the affected skin parts and operated sites, and percutaneous absorption of drugs. A pressure sensitive adhesive tape for skin generally has a structure that a pressure sensitive adhesive layer optionally containing a drug is formed on one side of a flexible base material.

Such a pressure sensitive adhesive tape for skin is required to (1) have good conformability to skin that permits conforming to the shape and movement of a skin surface applied, (2) prevent moisture by sweating from remaining therein so as to have excellent moisture permeability, (3) give neither pain nor separation of horny layer upon its peeling, (4) be able to retain tackiness to skin over a long period of time, and (5) cause none of dermal diseases such as rash, itch and erythema.

Since the adhesive tape is often stuck on the skin surface over a long period of time, however, it has involved a problem that troubles such as skin irritation always follow the skin surface covered therewith as side effects.

Various proposals have heretofore been made for lessening the troubles such as skin irritation. For example, there have been proposed (1) a method in which a crosslinked pressure sensitive adhesive layer comprising an acrylic ester polymer and a liquid component compatible with the polymer is formed on a base material, thereby lessening separation of corneocytes upon peeling (Japanese Patent Application Laid-Open No. 65224/1993), (2) a method in which moisture permeability is imparted to a base material and a pressure sensitive adhesive layer, thereby lightening dermal diseases and skin irritation (Japanese Patent Application Laid-Open Nos. 279251/1993, 157423/1995 and 275340/1995), (3) a method in which a base material composed of a water-absorbing polymer and a pressure sensitive adhesive containing a water-absorbing substance are used, thereby lightening skin irritation and separation of horny layer (Japanese Patent Application Laid-Open Nos. 16541/1994 and 206710/1995), (4) a method in which the amount of a monomer remaining in a pressure sensitive adhesive is reduced, thereby preventing the development of irritation, rash, itch, erythema, etc. (Japanese Patent Application Laid-Open No. 131022/1993), and (5) a method in which a stretchable base material is used, thereby imparting conformability to skin (Japanese Patent Application Laid-Open Nos. 138152/1995 and 117268/1996).

However, various factors are complicatedly entangled on the development of skin irritation by sticking of a pressure sensitive adhesive tape for skin, so that the mere improvement in a single factor or two factors does not result in a full solution of the problem. For example, when a measure to lighten skin irritation is adopted, such problems as tackiness and conformability to skin are deteriorated are easy to arise, and so it has been difficult to suitably balance the various characteristics with one another.

On the other hand, for example, a polyethylene film, ethylene-methyl methacrylate copolymer (EMMA) film, polyvinyl chloride film, polyurethane film, polyester elastomer film, polyvinyl alcohol film, microporous polyolefin film, nonwoven polyurethane fabric, nonwoven polyester elastomer fabric or the like is used as a base material used in a pressure sensitive adhesive tape for skin.

Among these base materials, films themselves such as the polyethylene film, EMMA film and polyvinyl chloride film do not have moisture permeability, and so holes are made therein by a perforator to impart the moisture permeability. However, such a film involves a problem that satisfactory moisture permeability is not given because the rate of holes bored by the perforation is at most several percent, and moreover a distance between individual holes is great and a portion, in which no hole is bored, has no moisture permeability.

The polyurethane film, polyester elastomer film, polyvinyl alcohol film, nonwoven polyurethane fabric, nonwoven polyester elastomer fabric, etc. involve a problem that they are too flexible in addition to their high prices. A pressure sensitive adhesive tape for skin, the base material of which is too flexible, wrinkles upon its application to a skin surface, and so its handling is difficult. Besides, the moisture permeability of the polyurethane film and polyvinyl alcohol film is markedly deteriorated when their thickness is increased to about 40 μm, and they scarcely exhibit the moisture permeability when their thickness reaches 60 μm or greater.

Some of microporous polyolefin films are known to have excellent moisture permeability as demonstrated by their water-vapor transmission rate of at least 2,500 $g/m^2 \cdot 24$ h, and they have good conformability to skin and are relatively cheap. Although many of the conventional microporous polyolefin films have an air permeability of 500 sec/100 cc or higher and are also small in film thickness and are hence suitable for use in paper diapers and sanitary products, however, they have been not satisfactory for base materials of pressure sensitive adhesive tapes for skin. An investigation by the present inventors have revealed that when a pressure sensitive adhesive layer is formed on the surface of a microporous polyolefin film having an air permeability of 500 sec/100 cc or higher, the water-vapor transmission rate thereof is markedly lowered, and so any pressure sensitive adhesive tape excellent in moisture permeability cannot be provided.

In order that a pressure sensitive adhesive tape for skin is hard to be steamed up, scarcely causes corneum separation and exhibits stable adhesive strength, it desirably has a water-vapor transmission rate of generally 500 $g/m^2 \cdot 24$ h or higher, preferably 700 $g/m^2 \cdot 24$ h or higher. When the microporous film described above is used as a base material, however, any pressure sensitive adhesive tape having satisfactory water-vapor transmission rate cannot be obtained. In addition, when the thickness of the microporous polyolefin film is too small, such a film involves a problem that it is too flexible as a base material. When the thickness thereof is made great, the water-vapor transmission rate thereof is further lowered when it is used in a pressure sensitive adhesive tape

DISCLOSURE OF THE INVENTION

It is an object of the present invention to provide a pressure sensitive adhesive tape for skin, in which the conformability to skin, moisture permeability and tackiness to skin thereof are all within proper ranges, these characteristics are balanced with one another at a high level, tackiness upon sweating or during sticking for a long period of time is stabilized, and pain, corneum separation and skin irritation upon its peeling are lightened to a great extent.

Another object of the present invention is to provide a pressure sensitive adhesive tape for skin, in which the conformability to skin, moisture permeability and tackiness to skin thereof are all within proper ranges, these characteristics are balanced with one another at a high level, tackiness upon sweating or during sticking for a long period of time is stabilized, and pain, corneum separation and skin irritation upon its peeling are lightened to a great extent.

A further object of the present invention is to provide a microporous film substrate suitable for use as a base material of such a pressure sensitive adhesive tape for skin having excellent various characteristics.

The present inventors have carried out an extensive investigation with a view toward overcoming the above-described problems involved in the prior art. As a result, it has been found that a pressure sensitive adhesive tape, which comprises a base material such as a film or nonwoven fabric high in moisture permeability and flexible, and a pressure sensitive adhesive layer formed from an acrylic pressure sensitive adhesive, rubber pressure sensitive adhesive, silicone pressure sensitive adhesive, vinyl ether pressure sensitive adhesive or the like on the base material, and has conformability to a stretchable film, water-vapor transmission rate and adhesive strength within respective specified ranges, has moderate conformability to skin, moisture permeability and tackiness to skin and is suitable for use as a pressure sensitive adhesive tape for skin. The pressure sensitive adhesive tape for skin has stable tackiness upon sweating or during sticking for a long period of time and scarcely causes pain, corneum separation and skin irritation upon its peeling.

The present inventors have also found that a microporous film formed from a resin composition comprising a polyolefin resin and an inorganic filler and having such selected characteristics that the thickness is 40 to 200 µm, the average pore size is 0.02 to 10 µm, the air permeability is 10 to 400 sec/100 cc, the water-vapor transmission rate is 1,000 to 20,000 g/ m²·24 h, and stresses at 15% elongation in the machine direction and transverse direction are both 0.5 to 15 N/15 mm is suitable for use as a base material of a pressure sensitive adhesive tape for skin. A pressure sensitive adhesive tape for skin having such excellent various characteristics as described above is provided by using this microporous film as a base material. The present invention has been led to completion on the basis of these findings.

According to the present invention, there is thus provided a pressure sensitive adhesive tape for skin, comprising a stretchable base material having good moisture permeability and a pressure sensitive adhesive layer formed on at least one side of the base material, wherein the adhesive tape has the following characteristics:

(a) the conformability to a stretchable film being at most 4.2 times as much as the stress of the stretchable film at 15% elongation;

(b) the water-vapor transmission rate being at least 500 g/m²·24 h; and (c) the adhesive strength to bakelite being at most 1.5 N/15 mm.

According to the present invention, there is also provided a base material of a pressure sensitive adhesive tape for skin, comprising a microporous film formed from a resin composition comprising a polyolefin resin and an inorganic filler, and having the following characteristics:

(1) the thickness being 40 to 200 µm;

(2) the average pore size being 0.02 to 10 µm;

(3) the air permeability being 10 to 400 sec/100 cc;

(4) the water-vapor transmission rate being 1,000 to 20,000 g/m²·24 h; and (5) the stresses at 15% elongation in the machine direction and transverse direction being both 0.5 to 15 N/15 mm.

Figure 1:
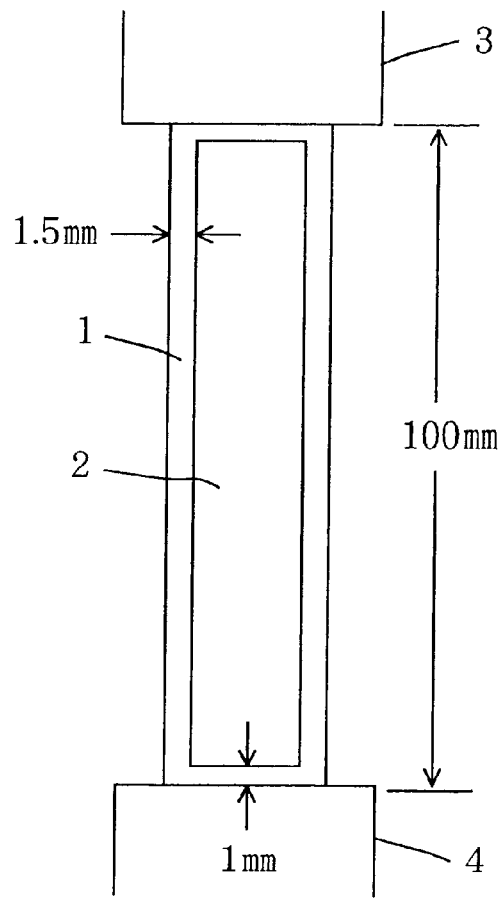
FIG. 1 illustrates a measuring method of the conformability of a pressure sensitive adhesive tape to a stretchable film.

BEST MODE FOR CARRYING OUT THE INVENTION (1) Base Material

As examples of a base material used in the pressure sensitive adhesive tape for skin according to the present invention, may be mentioned films or nonwoven fabrics high in moisture permeability and good in stretchability. The stress of the base material at 15% elongation can be used as an objective index to the stretchability thereof. The stresses at 15% elongation in the machine direction (MD) and transverse direction (MD) of the base material used in the present invention are both generally at most 15 N/15 mm, preferably at most 12 N/15 mm, more preferably at most 10 N/15 mm. The lower limit of the stress at 15% elongation of the base material is generally 0.5 N/15 mm, preferably 0.7 N/15 mm, more preferably 1 N/15 mm.

When the stress at 15% elongation of the base material falls within this range, a pressure sensitive adhesive tape easy to conform to the movement of a skin surface can be obtained. The stress at 15% elongation of the base material as used herein is a value measured as a stress as determined by elongating a specimen 15 mm in width and 150 mm in length by 15% at a crosshead interval of 100 mm and a crosshead speed of 300 mm/min by means of an Instron tensile tester in an atmosphere at a temperature of 23° C.±2° C. and a relative humidity of 65±5% in accordance with JIS K 7115.

The moisture permeability of the base material according to the present invention can be objectively evaluated by its water-vapor transmission rate as measured under conditions B (temperature: 40° C.; relative humidity: 90%) of JIS Z 0208. The water-vapor transmission rate of the base material used in the present invention is generally higher than 500 g/m²·24 h, preferably at least 700 g/m²·24 h, more preferably at least 1,000 g/m²·24 h. When the water-vapor transmission rate of the base material falls within the above range, a pressure sensitive adhesive tape which makes it difficult to cause skin irritation by effectively evaporating moisture generated by sweating during its sticking can be obtained. When the water-vapor transmission rate of the base material falls within a range of 1,000 to 20,000 g/m$^2$·24 h, good results can be yielded in many cases.

As specific examples of the stretchable base material having such moisture permeability, may be mentioned polyurethane films, polyester elastomer films, air-permeable polyolefin films, polyvinyl alcohol films, nonwoven polyurethane fabrics, nonwoven polyester elastomer fabrics and nonwoven thermoplastic polyolefin fabrics. The thickness of the base material is generally 40 to 200 μm, preferably 45 to 150 μm, more preferably 50 to 100 μm. If the thickness is too thin, the base material is too flexible, resulting in a pressure sensitive adhesive tape for skin which is hard to handle. If the thickness is too great, the flexibility of the base material is impaired, resulting in a pressure sensitive adhesive tape for skin deteriorated in conformability to skin.

Among the stretchable base materials having good moisture permeability, the air-permeable polyolefin films are preferred. More specifically, it is preferable to use a microporous film formed from a resin composition comprising a polyolefin resin and an inorganic filler as the base material for a low-irritative pressure sensitive adhesive tape for skin. As an example of a process for forming the microporous film, is mentioned a process in which the resin composition is used to form an unstretched film, and the film is then uniaxially or biaxially stretched into a stretched film.

As examples of the polyolefin resin, may be mentioned low density polyethylene, medium density polyethylene, high density polyethylene, linear low density polyethylene, very low density polyethylene, polypropylene, ethylene-propylene copolymers, ethylene-vinyl acetate copolymer and ionomer resins. The polyolefin resins include ethylene-α-olefin copolymers. Examples of the α-olefin include 1-butene, 3-methyl-1-butene, 4-methyl-1-pentene, 1-hexene, 1-octene and 1-decene.

These polyolefin resins may be either those obtained by using an ordinary Ziegler-Natta catalyst or those obtained by using a single site catalyst such as a metallocene catalyst or constraint geometry catalyst. The density of the polyolefin resin is generally about 0.89 to 0.97 g/Cm$^3$, and the melt index (MI) thereof is generally about 0.1 to 50 g/10 min. These polyolefin resins may be used either singly or in any combination thereof.

As examples of the inorganic filler, may be mentioned calcium carbonate, calcium oxide, aluminum oxide (alumina), titanium oxide, silica, clay, talc and aluminum sulfate. These inorganic fillers may be used either singly or in any combination thereof. The form of the inorganic filler may be optional, but it is preferably in a form such as a spheres, granule or indeterminate form. The average particle diameter of the inorganic filler is generally about 0.07 to 15 μm, preferably about 0.1 to 9 μm. When the average particle diameter falls within this range, the stretchability of the resulting microporous film becomes good, and the average pore size, air permeability, water-vapor transmission rate and the like of the film are easy to be controlled within the respective desired ranges.

The mixing proportion of the inorganic filler is generally about 50 to 250 parts by weight, preferably about 80 to 200 parts by weight per 100 parts by weight of the polyolefin resin. When the mixing proportion of the inorganic filler falls within this range, the various characteristics of the resulting microporous film can be controlled within the respect desired ranges.

The resin composition comprising the polyolefin resin and the inorganic filler may contain additives such as dispersing agents, heat stabilizers, ultraviolet absorbents, lubricants, pigments and antistatic agents as needed. Dispersing agents such as higher fatty acids having 10 to 22 carbon atoms, such as oleic acid, lauric acid, myristic acid, palmitic acid, stearic acid, linolic acid, linolenic acid and recinolic acid; and fatty acid esters (for example, purified castor oil) of a higher fatty acid having 10 to 22 carbon atoms with an aliphatic alcohol having 1 to 12 carbon atoms are particularly preferred because the stretchability, air permeability and soft feeling of the resulting microporous film can be enhanced, and the hand thereof can be made good. The dispersing agents may be used either singly or in any combination thereof. The dispersing agents are added in a proportion of generally 0.5 to 25 parts by weight, preferably 1 to 20 parts by weight per 100 parts by weight of the polyolefin resin.

In order to form the microporous film using the above-described resin composition, the resin composition is melt formed into an unstretched film (sheet) by means of T-die method, inflation method, or the like, and the film is then uniaxially or biaxially stretched into a stretched film. The unstretched film may be simultaneously biaxially stretched. No particular limitation is imposed on the stretching method. Uniaxial stretching includes roll stretching and oven stretching in a flat form, stretching in a tubular form, etc., and biaxial stretching includes tenter stretching in a flat form, inflation stretching and mandrel stretching in a tubular form, etc.

The draw ratio is generally 1.2 to 6 times, preferably 1.5 to 5 times, more preferably 2 to 3 times in at least one axial direction. In order to enhance dimensional accuracy, the stretched film may be heat treated under tension to heat set the film. Stretching temperature and other stretching conditions such as heat treating conditions may be suitably selected in accordance with the stretching conditions for ordinary polyolefin resins. By conducting the stretching, a microporous structure is formed in the resultant stretched film due to interfacial separation between the polyolefin resin and the inorganic filler, and the like.

In the present invention, the kind of the polyolefin resin, the kind and mixing proportion of the filler, the kinds and amounts of the additives such as the dispersing agent to be added, stretching conditions such as draw ratio, etc. are suitably controlled, thereby forming a microporous film having the following characteristics:

(1) the thickness being 40 to 200 μm;

(2) the average pore size being 0.02 to 10 μm;

(3) the air permeability being 10 to 400 sec/100 cc;

(4) the water-vapor transmission rate being 1,000 to 20,000 g/m$^2$·24 h; and (5) the stresses at 15% elongation in the machine direction and transverse direction being both 0.5 to 15 N/15 mm.

The thickness of the microporous film according to the present invention is 40 to 200 μm, preferably 45 to 150 μm, more preferably 50 to 100 μm. If the thickness is too thin, the microporous film is too flexible, resulting in a pressure sensitive adhesive tape for skin which is hard to handle. If the thickness is too great, the flexibility of the microporous film is impaired, resulting in a pressure sensitive adhesive tape for skin deteriorated in conformability to skin.

The average pore size of the microporous film according to the present invention is 0.02 to 10 μm, preferably 0.05 to 6 μm, more preferably 0.1 to 5 μm. The average pore size can be determined by taking a photograph of the microporous film through a scanning electron microscope, observing this photograph to measure the length of each pore, and calculating out an average value thereof.

The pore size is variedly distributed within a range of generally 0.01 to 20 μm. However, in many cases, it is at most 10 μm, thereby providing a microporous film with a great number of fine pores formed therein. If the average pore size is too small, the air permeability and water-vapor transmission rate of the microporous film are lowered. If the average pore size is too great, the flexibility of the microporous film is deteriorated.

The air permeability of the microporous film according to the present invention is 10 to 400 sec/100 cc, preferably 10 to 300 sec/100 cc, more preferably 30 to 280 sec/100 cc, particularly preferably 50 to 270 sec/100 cc. The air permeability can be determined in accordance with the testing method for air permeability (temperature: 23° C., relative humidity: 65%) prescribed in JIS P 8117. The air permeability means the time required until air (100 cc) under a fixed pressure passes through a film surface of a fixed area (645 $mm^2$) and a smaller value thereof indicates that the air permeability of a film is better.

If the air permeability of the microporous film is too high, only a pressure sensitive adhesive tape having a markedly low water-vapor transmission rate can be provided when such a microporous film is used as a base material for the pressure sensitive adhesive tape to apply a pressure sensitive adhesive to the surface thereof even when the water-vapor transmission rate thereof is high. If the air permeability thereof is too low, the flexibility thereof is easy to be impaired, and a pressure sensitive adhesive applied thereto is easy to penetrate into pores. When the air permeability of the microporous film falls within the above-described range, the water-vapor transmission rate of the resulting pressure sensitive adhesive tape can be controlled to at least 700 $g/m^2 \cdot 24$ h that is desirable for application to skin.

The water-vapor transmission rate of the microporous film according to the present invention is 1,000 to 20,000 $g/m^2 \cdot 24$ h, preferably 2,500 to 15,000 $g/m^2 \cdot 24$ h, more preferably 3,000 to 10,000 $g/m^2 \cdot 24$ h. If the water-vapor transmission rate of the microporous film according to the present invention is too low, the water-vapor transmission rate of the resulting pressure sensitive adhesive tape is lowered. If the water-vapor transmission rate is too high, the microporous film becomes brittle.

The stresses at 15% elongation (may also be referred to as tensile stresses at 15% elongation) in the machine direction (MD) and transverse direction (TD) of the microporous film according to the present invention are both 0.5 to 15 N/15 mm, preferably 0.7 to 12 N/15 mm, more preferably 1 to 10 N/15 mm. The flexibility of the microporous film can be objectively evaluated by measuring the stress at 15% elongation of the microporous film. When the stress at 15% elongation of the microporous film falls within the above range, a pressure sensitive adhesive tape easy to conform to the movement of a skin surface applied can be obtained. If the stress is too low, the microporous film becomes too flexible and unsuitable for use as a base material for a pressure sensitive adhesive tape for skin. If the stress is too high, the flexibility of the microporous film is lowered.

(2) Pressure Sensitive Adhesive

The pressure sensitive adhesive used in the pressure sensitive adhesive tapes according to the present invention is preferable such that is hard to separate corneocytes from a skin surface when the pressure sensitive adhesive tape is peeled therefrom and to damage the skin surface. As an index to a pressure sensitive adhesive having such adhesive properties, can be used the adhesive strength to bakelite of a pressure sensitive adhesive tape produced with the pressure sensitive adhesive.

The adhesive strength to bakelite of the pressure sensitive adhesive used in the present invention is at most 1.5 N/15 mm, preferably at most 1.4 N/15 mm. The lower limit of the adhesive strength to bakelite is generally 0.6 N/15 mm, preferably 0.8 N/15 mm. The adhesive strength to bakelite as used herein is a value obtained by measuring the adhesive strength of a pressure sensitive adhesive 15 mm in width to a bakelite panel in accordance with the 180 degree peeling method prescribed JIS Z 0237.

The pressure sensitive adhesive used in the present invention is preferably excellent in moisture permeability so as to provide a pressure sensitive adhesive tape having a water-vapor transmission rate of at least 500 $g/m^2 \cdot 24$ h, preferably at least 700 $g/m^2 \cdot 24$ h, more preferably at least 1,000 $g/m^2 \cdot 24$ h when a pressure sensitive adhesive layer is formed on the above-described base material. The upper limit of the water-vapor transmission rate of the pressure sensitive adhesive tape is generally about 5,000 $g/m^2 \cdot 24$ h. Any water-vapor transmission rate of the pressure sensitive adhesive tape too low forms the cause of the retention of mixture by sweating, separation of horny layer upon peeling, dermal diseases such as rash, itch and erythema, etc. The upper limit of the water-vapor transmission rate of the pressure sensitive adhesive tape is controlled by the air permeability and water-vapor transmission rate of the base material, the kind of the pressure sensitive adhesive tape, etc.

As the pressure sensitive adhesive used in the present invention, is preferred such a pressure sensitive adhesive that the shear deformation (mm/12×20 $mm^2 \cdot 2$ N·30 min) of the pressure sensitive adhesive is within a range of 0.15 to 1.20 mm from the viewpoint of the lightening of skin irritation. More specifically, as the pressure sensitive adhesive, is preferred that which is hard to impair the movement of a skin surface applied like the base material, from the viewpoint of providing a low-irritative pressure sensitive adhesive tape for skin. Such adhesive property of the pressure sensitive adhesive can be evaluated by the shear deformation of the pressure sensitive adhesive to the surface of a nonstretchable hard film [for example, a polyethylene terephthalate (PET) film coated with a primer] subjected to a primer treatment. The shear deformation of the pressure sensitive adhesive tape as used in the present invention is preferably 0.17 to 1.0 mm, more preferably 0.20 to 0.50 mm. If the shear deformation of the pressure sensitive adhesive of the pressure sensitive adhesive tape is to small, skin irritation becomes great. If the shear deformation of the pressure sensitive adhesive is too great, the retention of the pressure sensitive adhesive on a skin surface and the like are easy to occur.

As examples of the pressure sensitive adhesive used in the pressure sensitive adhesive tapes according to the present invention, may be mentioned acrylic pressure sensitive adhesives, rubber pressure sensitive adhesives, silicone pressure sensitive adhesives and vinyl ether pressure sensitive adhesives. Among these pressure sensitive adhesives, acrylic pressure sensitive adhesives obtained by (co) polymerizing a monomer or monomer mixture comprising a (meth)acrylic ester as a main monomer are preferred from the viewpoint of initial tack or skin irritation. Acrylic pressure sensitive adhesives comprising, as an adhesive component, an acrylic copolymer obtained by using an alkoxypolyalkylene glycol (meth)acrylate and a hydroxyl group- or carboxyl group-containing monomer as comonomers in combination are particularly preferred from the viewpoint of stable tackiness to skin, high moisture permeability, lessening of corneum separation and lightening of pain in the skin upon peeling.

More specifically, as preferable acrylic pressure sensitive adhesives, may be mentioned copolymers of (1) 50 to 97.5 wt. %, preferably 70 to 95 wt. % of an alkyl (meth)acrylate having an alkyl group having 4 to 12 carbon atoms, (2) 2 to 49.5 wt. %, preferably 4 to 29 wt. % of an alkoxypolyalkylene glycol (meth)acrylate, and (3) 0.5 to 15 wt. %, preferably 1 to 10 wt. % of a hydroxyl group- or carboxyl group-containing monomer. The copolymers may be those obtained by copolymerizing a still further copolymerizable vinyl monomer within a range of about 0 to 30 wt. %.

As examples of the alkyl (meth)acrylate having an alkyl group having 4 to 12 carbon atoms, may be mentioned n-butyl acrylate, isobutyl acrylate, t-butyl acrylate, 2-ethylhexyl acrylate, n-octyl acrylate, isooctyl acrylate, isononyl acrylate, decyl acrylate, dodecyl acrylate, n-butyl methacrylate, isobutyl methacrylate, t-butyl methacrylate, 2-ethylhexyl methacrylate, n-octyl methacrylate, isooctyl methacrylate, isononyl methacrylate, decyl methacrylate and dodecyl methacrylate. Among these, 2-ethylhexyl acrylate, n-octyl acrylate, isooctyl acrylate and isononyl acrylate are preferred. These alkyl (meth)acrylates may be used either singly or in any combination thereof.

The alkoxypolyalkylene glycol (meth)acrylate is a (meth) acrylic ester represented by the following formula (1):

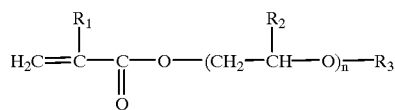

(1)

wherein $R_1$ and $R_2$ are independently a hydrogen atom or a methyl group, $R_3$ is an alkyl group having 1 to 20 carbon atoms, and n is an integer of 2 to 12.

Specific examples of the monomer represented by the formula (1) include methoxydiethylene glycol acrylate ($R_1$=H, $R_2$=H, $R_3$=$CH_3$, n=2), methoxydiethylene glycol methacrylate ($R_1$=$CH_3$, $R_2$=H, $R_3$=$CH_3$, n=2), methoxydipropylene glycol acrylate ($R_1$=H, $R_2$=$CH_3$, $R_3$=$CH_3$, n=2), methoxydipropylene glycol methacrylate ($R_1$=$CH_3$, $R_2$=$CH_3$, $R_3$=$CH_3$, n=2), ethoxydiethylene glycol acrylate ($R_1$=H, $R_2$=H, $R_3C_2H_5$, n=2), ethoxy-diethylene glycol methacrylate ($R_1$=$CH_3$, $R_2$=H, $R_3$ $C_2H_5$, n=2), ethoxydipropylene glycol acrylate ($R_1$=H, $R_2$=$CH_3$, $R_3$=$C_2H_5$, n=2), ethoxydipropylene glycol methacrylate ($R_1$=$CH_3$, $R_2$=$CH_3$, $R_3$=$C_2H_5$, n=2), methoxytriethylene glycol acrylate ($R_1$=H, $R_2$=H, $R_3$=$CH_3$, n=3), methoxy-triethylene glycol methacrylate ($R_1$=$CH_3$, $R_2$=H, $R_3$=$CH_3$, n=3), methoxytripropylene glycol acrylate ($R_1$=H, $R_2$=$CH_3$, $R_3$=$CH_3$, n=3), methoxytripropylene glycol methacrylate ($R_1$=$CH_3$, $R_2$=$CH_3$, $R_3$=$C_2H_5$, n=3), methoxy-polyethylene glycol acrylate ($R_1$=H, $R_2$=H, $R_3$=$CH_3$, n=4 to 10), methoxypolyethylene glycol methacrylate ($R_1$=$CH_3$, $R_2$=H, $R_3$=$CH_3$, n=4 to 10), methoxypolypropylene glycol acrylate ($R_1$=H, $R_2$=$CH_3$, $R_3$=$CH_3$, n=4 to 10) and methoxypolypropylene glycol methacrylate ($R_1$=$CH_3$, $R_2$=$CH_3$, $R_3$=$CH_3$, n=4 to 10).

As examples of the hydroxyl group- or carboxyl group-containing monomer, may be mentioned hydroxyalkyl (meth)acrylates and carboxyalkyl (meth)acrylates. Specific examples of these monomers include 2-hydroxyethyl acrylate, 2-carboxyethyl acrylate, 2-hydroxypropyl acrylate, 2-carboxypropyl acrylate, 3-hydroxypropyl acrylate, 3-carboxypropyl acrylate, 4-hydroxybutyl acrylate, 4-carboxybutyl acrylate, 2-hydroxyethyl methacrylate, 2-carboxyethyl methacrylate, 2-hydroxypropyl methacrylate, 2-carboxypropyl methacrylate, 3-hydroxypropyl methacrylate, 3-carboxypropyl methacrylate, 4-hydroxybutyl methacrylate and 4-carboxybutyl methacrylate.

As examples of the hydroxyl group-containing monomer, may be mentioned hydroxyl group-containing (meth)acrylic esters represented by the formula (2):

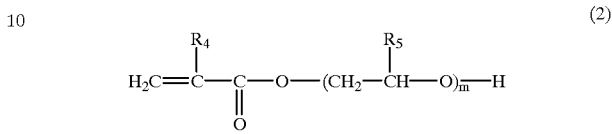

(2)

wherein $R_4$ and $R_5$ are independently a hydrogen atom or a methyl group, and m is an integer of 2 to 12, such as polyethylene glycol (meth)acrylates and polypropylene glycol (meth)acrylates.

As examples of the carboxyl group-containing monomer, ay be mentioned carboxyl group-containing (meth)acrylic esters represented by the formula (3):

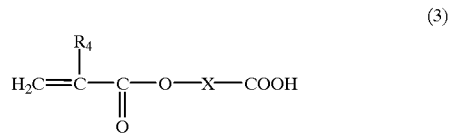

(3)

wherein $R_6$ is a hydrogen atom or a methyl group, and X is a divalent organic group having at least 2 carbon atoms and may contain a heteroatom such as an oxygen, nitrogen or sulfur atom.

In the formula (3), the number of carbon atoms in X is preferably 2 to 50, more preferably 2 to 30. The heteroatom is an oxygen atom in many cases. As specific examples of X, may be mentioned linear or branched alkylene groups having at least two carbon atoms, —$R_7$—OCO—$R_8$ (wherein $R_7$ and $R_8$ are alkylene groups) and —$R_9$—OCO—$R_{10}$—OCO—$R_{11}$— (wherein $R_9$, $R_{10}$ and $R_{11}$ are alkylene groups). Specific examples of the carboxyl group-containing (meth)acrylic esters represented by the formula (3) include 2-carboxyethyl acrylate, 2-acryloyloxyethylsuccinic acid and ω)-carboxypolycaprolactone acrylate.

As examples of the still further copolymerizable vinyl monomer, may be mentioned alkyl (meth)acrylates such as methyl acrylate, ethyl acrylate, isopropyl acrylate, methyl methacrylate, ethyl methacrylate, isopropyl methacrylate, tridecyl acrylate and tridecyl methacrylate; carboxyl group-containing monomers such as acrylic acid, methacrylic acid, maleic acid, maleic anhydride and itaconic acid; (meth) acrylamides and derivatives thereof such as acrylamide, methacrylamide and N-methylolacrylamide; epoxy group-containing monomer such as glycidyl acrylate and glycidyl methacrylate; vinyl esters such as vinyl acetate; unsaturated nitrites such as acrylonitrile and methacrylonitrile; and vinyl aromatic compounds such as styrene.

To the pressure sensitive adhesives used in the present invention, may be added general-purpose various additives if desired. Into the pressure sensitive adhesives, may be incorporated percutaneously absorbable drugs if desired. Examples of the percutaneously absorbable drugs include drugs for angina pectoris, corticosteroids, analgesic-antiphlogestic drugs, hypnotic analgesics, anti-inflammatory drugs, antiallergic drugs, antihistaminics, coronary vasodilators, antibacterial drugs, humectants, vitamins, antitussives, anesthetic drugs, antitumor drugs and perfume bases. These drugs are added in affective amounts as needed.

(3) Pressure Sensitive Adhesive Tape for Skin

The pressure sensitive adhesive tapes for skin according to the present invention can be produced by applying a pressure sensitive adhesive to at least one side of a stretchable base material having good moisture permeability in accordance with a method known per se in the art. The pressure sensitive adhesive may be applied to a separator to transfer it to the base material. In order to apply the pressure sensitive adhesive, it is only necessary to apply a solution with a base polymer and optional additive ingredients uniformly dissolved or dispersed in an organic solvent to the base material or separator and dry it. The thickness of the pressure sensitive adhesive layer is generally 20 to 60 μm, preferably 30 to 50 μm.

The pressure sensitive adhesive tapes for skin according to the present invention have the following various characteristics:

(a) the conformability to a stretchable film being at most 4.2 times, preferably at most 4.0 times, more preferably at most 3.8 times, often 2.4 to 4.2 times as much as the stress of the stretchable film at 15% elongation;

(b) the water-vapor transmission rate being at least 500 g/m$^2$·24 h, preferably 700 to 5,000 g/m$^2$·24 h, more preferably 750 to 3,000 g/m$^2$·24 h, particularly preferably 800 to 2,000 g/m$^2$·24 h; and (c) the adhesive strength to bakelite being at most 1.5 N/15 mm, preferably 0.6 to 1.5 N/15 mm, more preferably 0.8 to 1.4 N/15 mm.

In order to determine the conformability of the pressure sensitive adhesive tape to the stretchable film, a pressure sensitive adhesive tape sample is stuck on a stretchable film to measure a stress of the pressure sensitive adhesive tape sample when the stretchable film is elongated by 15% at a rate of 100 mm/min by means of an Instron tensile tester. The measured value of the stress is the conformability of the pressure sensitive adhesive tape to the stretchable film. The measured value of the stress is divided by the stress at 15% elongation of the stretchable film to calculate out a quotient. The quotient must be 4.2 times or lower. In Examples and Comparative Examples, a polyurethane film (thickness: 27 μm) the stress at 15% elongation of which is 0.84 N/15 mm was used as the stretchable film because the polyurethane film is similar to the condition of the skin of a human body. The conformability of the pressure sensitive adhesive tape to skin can be objectively evaluated by this value (quotient). The conformability of the pressure sensitive adhesive tape according to the present invention to skin can be determined by actually applying it to the skin of a human body. However, since the skin of the human body varies with the individual, such conformability to the stretchable film is used as an objective index. The stress of the pressure sensitive adhesive tape as measured by the above-described measuring method generally falls within a range of 2.5 to 3.5 N/15 mm (quotient=3.0 to 4.2 times).

The pressure sensitive adhesive tapes according to the present invention are desirably such that (d) the shear deformation (mm/12×20 mm$^2$·2 N·30 min) of the pressure sensitive adhesive is within a range of preferably 0.15 to 1.20 mm, more preferably 0.17 to 1.0 mm, particularly preferably 0.20 to 0.50 mm from the viewpoint of the lessening of skin irritation and retention of the pressure sensitive adhesive on a skin surface.

Since the pressure sensitive adhesive tapes for skin according to the present invention have such various characteristics, they have features that the conformability to skin is good, the retention of moisture during its sticking is little, the tackiness upon sweating or during sticking for a long period of time is good, and pain, corneum separation and skin irritation upon peeling are little. Accordingly, the pressure sensitive adhesive tapes for skin according to the present invention can be used with the object of skin protection such as protection of the affected skin parts and operated sites, percutaneous absorption of drugs, etc.

EXAMPLES

The present invention will hereinafter be described more specifically by the following Examples and Comparative Examples. All designations of "part" or "parts" and "%" as will be used in the following examples and comparative examples mean part or parts by weight and % by weight unless expressly noted.

Physical properties, characteristics and performance of base materials and pressure sensitive adhesive tapes were determined in accordance with the following respective methods:

1. Base Material (1) Average Pore Size

An average value (unit: μm) of lengths of pores measured through a scanning electron microscope was calculated out to regard it as an average pore size (n=10). The forms of pores include various forms such as ellipse, rhombus, rectangle and polygon. However, the length means a length of the longest diameter or diagonal line. The measuring temperature is ordinary temperature (18 to 27° C.).

(2) Air Permeability

The time (unit: sec/100 cc) required until air (100 cc) under a fixed pressure passes through a film surface of a fixed area (645 mm$^2$) was measured in accordance with the testing method for air permeability prescribed in JIS P 8117 (n=3). The measurement was conducted under an atmosphere at a temperature of 23±2° C. and a relative humidity of 65±5%.

(3) Water-Vapor Transmission Rate

One side of a film sample of 36 cm$^2$ was adjusted at a temperature of 40° C. and a relative humidity of 90% according to the conditions B (temperature: 40° C.; relative humidity: 90%) of JIS Z 0208, and about 16 g of a moisture absorbent (calcium chloride) were placed on another side to cause moisture passed through the film to be absorbed, whereby a weight change of calcium chloride was converted into a value per 1 m$^2$ and 24 hours to regard its value as a water-vapor transmission rate (n=3).

(4) Stress at 15% Elongation

A stress load (sample width: 15 mm; crosshead interval: 100 mm; crosshead speed: 300 mm/min) at the time a sample was elongated by 15% by means of a tensile tester in accordance with JIS K 7115 was measured. The measurement was conducted in an atmosphere at a temperature of 23±2° C. and a relative humidity of 65±5%.

2. Characteristics of Pressure Sensitive Adhesive Tape (1) Conformability to Stretchable Film As illustrated in FIG. 1, a polyurethane film 1 (thickness: 27 μm) the stress at 15% elongation of which was 0.84 N/15 mm was cut into a size of 18 mm×150 mm and fixed by chucks 3 and 4 of an Instron tensile tester in such a manner that a crosshead interval is 100 mm. A pressure sensitive adhesive tape 2 cut into a size of 15 mm×98 mm was stuck on the polyurethane film 1 to measure a stress of the pressure sensitive adhesive tape 2 at the time the polyurethane film 1 was elongated by 15% at a crosshead speed of 100 mm/min. This stress was regarded as the conformability of the pressure sensitive adhesive tape to the stretchable film to compare it with the stress of the polyurethane film at 15% elongation. The measurement was conducted in an atmosphere at a temperature of 23° C. and a relative humidity of 65%.

(2) Adhesive Strength to Bakelite

The adhesive strength of each pressure sensitive adhesive tape 15 mm in width to a bakelite panel was measured in accordance with the 180 degree peeling method prescribed JIS Z 0237. The measurement was conducted in an atmosphere at a temperature of 23±2° C. and a relative humidity of 65±5%.

(3) Water-Vapor Transmission Rate

The water-vapor transmission rate of each pressure sensitive adhesive tape was measured under the conditions B (temperature: 40° C.; relative humidity: 90%) of JIS Z 0208.

(4) Shear Deformation of Pressure Sensitive Adhesive

The shear deformation of a pressure sensitive adhesive means a shear deformation of the pressure sensitive adhesive as measured in a state that the surface of a nonstretchable hard film such as PET #36 was subjected to a primer treatment (for example, polyester resin "Vylon 30SS", product of Toyobo Co., Ltd.; applied in a thickness of about 3 µm) to remove the interfacial slip of the pressure sensitive adhesive of a pressure sensitive adhesive tape (with an adherend).

Figure 2:
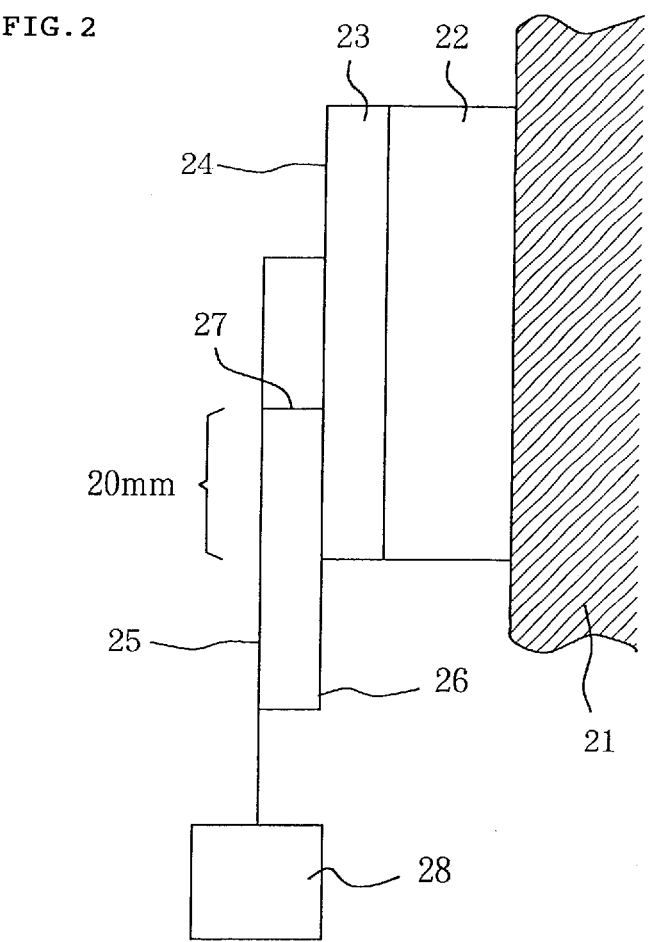
FIG. 2 illustrates a measuring method of the shear deformation of a pressure sensitive adhesive.

More specifically, as illustrated in FIG. 2, bakelite (or glass plate) 22 was fixed to a vertical surface of a support 21, and a PTE film 23 subjected to a primer treatment was bonded to the surface thereof with the primer treated surface 24 out. A pressure sensitive adhesive tape 25 was stuck at the side of the pressure sensitive adhesive layer 26 on the primer treated surface 24. A cut 27 was made in the pressure sensitive adhesive tape into a state that an area of 12×20 mm² of the pressure sensitive adhesive layer was stuck on the primer treated surface. A load 28 of 2 N was applied to the lower end of the adhesive tape 25. After leaving the adhesive tape 25 to stand for 30 minutes in this loaded state, the shear deformation of the adhesive layer at the cut portion was read through a microscope equipped with a scale to regard it as the shear deformation of the pressure sensitive adhesive (n=3).

Figure 3:
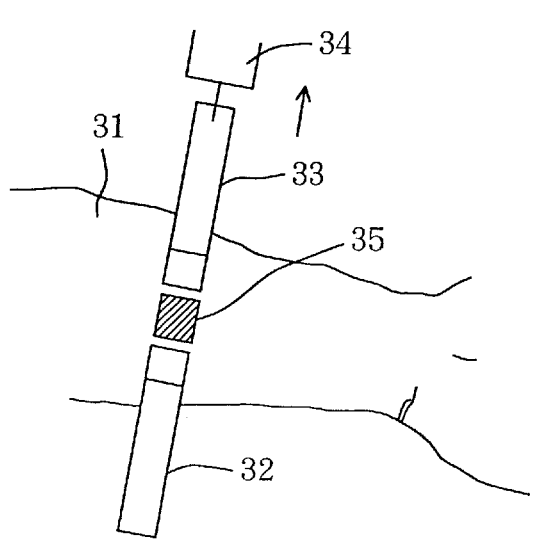
FIG. 3 illustrates a measuring method of the conformability of a pressure sensitive adhesive tape to skin.

3. Performance Evaluation of Pressure Sensitive Adhesive Tape (1) Conformability to Skin As illustrated in FIG. 3, 2 nonstretchable films 32, 33 in the form of a strip 15 mm in width were stuck at an interval of 20 mm on inner lower arms of 6 adult men, an end of one nonstretchable film 32 was fixed, and an end of the other nonstretchable film 33 was connected to a strain gauge 34 (digital force gauge). A pressure sensitive adhesive tape 35 of 15 mm×18 mm was stuck each at an interval of 1 mm between the two nonstretchable films to evaluate the stress at 15% elongation of the adhesive tape as an index to the conformability to skin in comparison with the viscoelasticity of the skin. The measurement was conducted in an atmosphere at a temperature of 23±2° C. and a relative humidity of 65±5%.

(2) Tackiness to Skin, Retention of Moisture and Pain Upon Peeling

Two strips of each pressure sensitive adhesive tape of 15 mm×70 mm were stuck in a transverse direction on inner lower arms of 8 adult men. The tackiness to the skin was measured at a peeling angle of 90° by means of an Instron tensile tester after 1 hour and 24 hours. With respect to the sample stuck for 24 hours, the retention of moisture and pain upon peeling and skin irritation after 1 hour from the peeling were evaluated. With respect to the retention of moisture, the conductivity of the epidermal horny layer before and after sticking was measured by means of SKICON 200 (manufactured by IBS) to evaluate that moisture was retained when the conductivity of the epidermal horny layer markedly increased. With respect to the pain upon peeling, inquiry was made at 4 ranks (0: no pain, 1: light pain, 2: strong pain, 3: unbearable pain) to express it by an average score.

(3) Skin Irritation Index

Each pressure sensitive adhesive tape 25 mm in diameter was stuck on inner lower arms of 10 adult men. The adhesive tape was peeled after 24 hours from the sticking to evaluate skin irritation after 1 hour from the peeling in accordance with the Japanese standard.

The Japanese standard is a standard prescribed by the Japanese patch test research group. More specifically, weights of 0, 0.5, 1, 2, 3 and 4 points were given to the following standard, −, ±, +, ++, +++and ++++, respectively, to multiply an average value of the evaluation results of the respective subjects by 100 to express the value thereof as an skin irritation index.

<Criterion>

−: Not reacted,

±: Light erythema,

+: Erythema,

++: Erythema +edema,

+++: Erythema +edema +papule,

++++: Erythema +edema +papule, serous papule, vesicle.

Example 1

An acrylic copolymer obtained by copolymerizing isononyl acrylate/methoxynonaethylene glycol acrylate/nonaethylene glycol methacrylate (83 parts/16 parts/1 part) was used as a pressure sensitive adhesive to prepare a pressure sensitive adhesive solution [solvent: toluene/ethyl acetate =7/3 (weight ratio); concentration: 30 wt. %] with 0.6 parts of Coronate L (product of Nippon Polyurethane Industry Co., Ltd.) added to 100 parts (solid content) of the copolymer.

This pressure sensitive adhesive solution was applied to a separator the surface of which had been subjected to a silicone treatment, so as to give a dry coating thickness of 38 µm, and dried at 120° C. for 3 minutes. Thereafter, a microporous polyolefin film having a thickness of 80 µm was laminated as a base material on the surface of the pressure sensitive adhesive layer, and aging was conducted at 50° C. for a week to produce a pressure sensitive adhesive tape for skin.

Example 2

A pressure sensitive adhesive tape for skin was produced in the same manner as in Example 1 except that the hydroxyl group-containing monomer among the monomer components of the pressure sensitive adhesive was changed to ethylene glycol methacrylate.

Comparative Example 1

An acrylic copolymer obtained by copolymerizing isononyl acrylate/methoxynonaethylene glycol acrylate/nonaethylene glycol methacrylate (83 parts/16 parts/1 part) was used as a pressure sensitive adhesive to prepare a pressure sensitive adhesive solution [solvent: toluene/ethyl acetate=7/3 (weight ratio); concentration: 30 wt. %] with 0.6 parts of Coronate L (product of Nippon Polyurethane Industry Co., Ltd.) added to 100 parts (solid content) of the copolymer.

This pressure sensitive adhesive solution was applied to a separator the surface of which had been subjected to a silicone treatment, so as to give a dry coating thickness of 38 μm, and dried at 120° C. for 3 minutes. Thereafter, an EMMA (ethylene-methyl methacrylate copolymer) film having a thickness of 100 μm was laminated as a base material on the surface of the pressure sensitive adhesive layer, and aging was conducted at 50° C. for a week to produce a pressure sensitive adhesive tape for skin.

Comparative Example 2

An isononyl acrylate/acrylic acid (98 parts/2 parts) copolymer was used as a pressure sensitive adhesive to prepare a pressure sensitive adhesive solution [solvent: toluene/ethyl acetate=7/3 (weight ratio); concentration: 30 wt. %]. This pressure sensitive adhesive solution was applied to a separator the surface of which had been subjected to a silicone treatment, so as to give a dry coating thickness of 38 μm, and dried at 120° C. for 3 minutes. Thereafter, a nonwoven rayon fabric having a thickness of 100 μm was laminated as a base material on the surface of the pressure sensitive adhesive layer, and aging was conducted at 40° C. for a week to produce a pressure sensitive adhesive tape for skin.

Comparative Example 3

An isononyl acrylate/acrylic acid (96 parts/4 parts) copolymer was used as a pressure sensitive adhesive to prepare a pressure sensitive adhesive solution [solvent: toluene/ethyl acetate=7/3 (weight ratio); concentration: 30 wt. %]. This pressure sensitive adhesive solution was applied to a separator the surface of which had been subjected to a silicone treatment, so as to give a dry coating thickness of 38 μm, and dried at 120° C. for 3 minutes. Thereafter, a polyethylene film having a thickness of 120 μm was laminated as a base material on the surface of the pressure sensitive adhesive layer, and aging was conducted at 40° C. for a week to produce a pressure sensitive adhesive tape for skin.

The physical properties of the respective base materials used in Examples 1 and 2, and Comparative Examples 1 to 3, the characteristics of the resultant respective pressure sensitive adhesive tapes, and the results of performance evaluation thereof are shown in Tables 1, 2 and 3, respectively.

TABLE 1

Base material

| | Thickness (μm) | Stress at 15% elongation (N/15 mm) MD | Stress at 15% elongation (N/15 mm) TD | Average pore size (μm) | Air permeability (sec/100 cc) | Water-vapor transmission rate (g/m² · 24 h) |
|---|---|---|---|---|---|---|
| Ex. 1 | 80 | 7.8 | 2.1 | 1.4 | 210 | 4290 |
| Ex. 2 | 80 | 7.8 | 2.1 | 1.4 | 210 | 4290 |
| Comp. Ex. 1 | 100 | 6.1 | 5.9 | Having no pore | — | 10 |
| Comp. Ex. 2 | 100 | ND | ND | ND | 0.3 | 7920 |
| Comp. Ex. 3 | 120 | 11.6 | 11.5 | Having no pore | — | 10 |

TABLE 2

Characteristics of pressure sensitive adhesive tape

| | Conformability to stretchable film (*1) N/15 mm | Conformability to stretchable film (*1) Quotient | Water-vapor transmission rate (g/m² · 24 h) | Adhesive strength to bakelite (N/15 mm) | Shear deformation of adhesive (mm/12 × 20 mm² · 2N · 30 min) |
|---|---|---|---|---|---|
| Ex. 1 | 3.08 | 3.66 | 1030 | 1.1 | 0.20 |
| Ex. 2 | 3.21 | 3.82 | 900 | 1.0 | 0.30 |
| Comp. Ex. 1 | 3.19 | 3.79 | 0 | 0.9 | 0.30 |
| Comp. Ex. 2 | 4.65 | 5.53 | 5100 | 2.5 | 0.10 |
| Comp. Ex. 3 | 4.47 | 5.32 | 0 | 5.2 | 0.10 |

(Note)
*1: The stress at 15% elongation of the stretchable film is 0.84 N/15 min. The quotient is a value obtained by dividing the conformability (value of stress) of each pressure sensitive adhesive tape to the stretchable film by the stress at 15% elongation of the stretchable film.

TABLE 3

Performance evaluation of pressure sensitive adhesive tape

| | Conformability to skin (*2) (N/15 mm) | Retention of moisture (μS) | Adhesive strength (N/15 mm) After 1 hr. | Adhesive strength (N/15 mm) After 24 hr. | Pain upon peeling | Skin irritation index |
|---|---|---|---|---|---|---|
| Ex. 1 | 0.71 | 100 | 0.7 | 0.7 | 0.3 | 20 |
| Ex. 2 | 0.69 | 110 | 0.8 | 0.7 | 0.3 | 20 |
| Comp. Ex. 1 | 0.70 | 270 | 0.6 | 0.3 | 0.0 | 20 |
| Comp. Ex. 2 | 0.86 | 40 | 1.0 | 1.9 | 0.5 | 30 |
| Comp. Ex. 3 | 0.84 | 520 | 1.5 | 0.5 | 0.9 | 30 |

(Note)
*2: The stress (skin viscoelasticity) of the skin at 15% elongation is 0.31 N/15 mm.

Example 3

An acrylic copolymer obtained by copolymerizing isononyl acrylate/methoxynonaethylene glycol acrylate/nonaethylene glycol methacrylate (83 parts/16 parts/1part) was used as a pressure sensitive adhesive to prepare a pressure sensitive adhesive solution [solvent: toluene/ethyl acetate=3/1 (weight ratio); concentration: 30 wt. %] with 0.6 parts of Coronate L (product of Nippon Polyurethane Industry Co., Ltd.) added to 100 parts (solid content) of the copolymer (Pressure Sensitive Adhesive ①). This pressure sensitive adhesive solution was applied to a separator the surface of which had been subjected to a silicone treatment, so as to give a dry coating thickness of 38 μm, and dried at 120° C. for 3 minutes.

To 100 parts of linear low density polyethylene (density=0.915 g/cm³), were added 120 parts of calcium carbonate having an average particle diameter of 1.8 μm, 1.2 parts of oleic acid and 8 parts of purified castor oil. The mixture was fully mixed and extruded into a strand at 200° C. from a twin-screw extruder to prepare pellets. The pellets were melt extruded into a sheet at a resin temperature of 210° C. through a T-die of an extruder to obtain an unstretched sheet having a thickness of about 400 μm. The unstretched sheet was reheated, biaxially stretched each at a draw ratio of about 3 times in both directions of MD and TD at a stretching temperature of 85° C. by a tenter stretching process and cooled by a cooling roll to obtain a biaxially stretched film (Base Material A) having a thickness of 53 µm. The biaxially stretched film was subjected to a corona discharge treatment at one surface thereof and laminated on the surface of the pressure sensitive adhesive layer applied to the separator, and aging was conducted at 50° C. for a week to produce a ressure sensitive adhesive tape for skin.

Example 4

With 100 parts of an ethylene-l-hexene copolymer density=0.920 g/cm$^3$), were mixed 160 parts of calcium arbonate having an average particle diameter of 1.1 µm, 1.2 parts of oleic acid and 7.8 parts of purified castor oil for 5 minutes in a super mixer. The resultant mixture was then extruded into a strand at 200° C. from a twin-screw extruder, and the extrudate was chopped into pellets. The pellets were melt extruded into a sheet at a resin temperature of 210° C. through a T-die of an extruder to obtain an unstretched sheet having a thickness of about 80 µm. The unstretched sheet was reheated, uniaxially stretched at a draw ratio of about 2 times at a stretching temperature of 85° C. by a roll stretching process to form a uniaxially stretched film (Base Material B) having a thickness of 50 µm.

A pressure sensitive adhesive tape for skin was produced in the same manner as in Example 3 except that the uniaxially stretched film formed above was used as a base material.

Example 5

With 100 parts of a mixture of 75 parts of an ethylene-1-butene copolymer (density=0.923 g/cm$^3$) and 25 parts of high-pressure-produced low density polyethylene (density= 0.925 g/cm$^3$), were mixed 120 parts of calcium carbonate having an average particle diameter of 1.2 µm, 1.2 parts of oleic acid and 6 parts of purified castor oil for 5 minutes in a super mixer. The resultant mixture was then extruded into a strand at 200° C. from a twin-screw extruder, and the extrudate was chopped into pellets. The pellets were melt extruded into a sheet at a resin temperature of 210° C. through a T-die of an extruder to obtain an unstretched sheet having a thickness of about 120 µm. The unstretched sheet was reheated, uniaxially stretched at a draw ratio of about 2 times at a stretching temperature of 85° C. by a roll stretching process to form a uniaxially stretched film (Base Material C) having a thickness of 82 µm.

A pressure sensitive adhesive tape for skin was produced in the same manner as in Example 3 except that the uniaxially stretched film formed above was used as a base material.

Example 6

An acrylic copolymer obtained by copolymerizing isononyl acrylate/methoxynonaethylene glycol acrylate/2-carboxyethyl acrylate (83 parts/15 parts/2 parts) was used as a pressure sensitive adhesive to prepare a pressure sensitive adhesive solution [solvent: toluene/ethyl acetate=3/1 (weight ratio); concentration: 30 wt. %] with 0.06 parts of TETRAD-X (product of Mitsubishi Gas Chemical Company, Inc.) added to 100 parts (solid content) of the copolymer (Pressure Sensitive Adhesive ②).

A pressure sensitive adhesive tape for skin was produced in the same manner as in Example 3 except that this pressure sensitive adhesive solution was used.

Example 7

An acrylic copolymer obtained by copolymerizing isononyl acrylate/methoxynonaethylene glycol acrylate/2-carboxyethyl acrylate (81 parts/15 parts/4 parts) was used as a pressure sensitive adhesive to prepare a pressure sensitive adhesive solution [solvent: toluene/ethyl acetate=3/1 (weight ratio); concentration: 30 wt. %] with 0.08 parts of TETRAD-X (product of Mitsubishi Gas Chemical Company, Inc.) added to 100 parts (solid content) of the copolymer (Pressure Sensitive Adhesive ③). A pressure sensitive adhesive tape for skin was produced in the same manner as in Example 3 except that this pressure sensitive adhesive solution was used.

Example 8

An acrylic copolymer obtained by copolymerizing isononyl acrylate/methoxynonaethylene glycol acrylate/nonaethylene glycol methacrylate (83 parts/16 parts/1 part) was used as a pressure sensitive adhesive to prepare a pressure sensitive adhesive solution [solvent: toluene/ethyl acetate=3/1 (weight ratio); concentration: 30 wt. %] with 0.6 parts of Coronate L (product of Nippon Polyurethane Industry Co., Ltd.) added to 100 parts (solid content) of the copolymer (Pressure Sensitive Adhesive ④). pressure sensitive adhesive tape for skin was produced in the same manner as in Example 3 except that this pressure sensitive adhesive solution was used.

Comparative Example 4

A pressure sensitive adhesive tape for skin was produced in the same manner as in Example 8 except that Porum PN70 (Base Material a; product of Tokuyama Co., Ltd.) which is a microporous polyolefin film formed from a resin composition containing polyethylene and an inorganic filler was used as a base material.

Comparative Example 5

A pressure sensitive adhesive tape for skin was produced in the same manner as in Comparative Example 4 except that Porum PH70 (Base Material b; product of Tokuyama Co., Ltd.) which is a microporous polyolefin film formed from a resin composition containing polyethylene and an inorganic filler was used as a base material.

Comparative Example 6

A pressure sensitive adhesive tape for skin was produced in the same manner as in Comparative Example 4 except that NF Sheet NG100 (Base Material c; product of Tokuyama Co., Ltd.) which is a microporous polyolefin film formed from a resin composition containing polypropylene and an inorganic filler was used as a base material.

Comparative Example 7

An acrylic copolymer obtained by copolymerizing isononyl acrylate/acrylic acid (96 parts/4 parts) was used as a pressure sensitive adhesive to prepare a pressure sensitive adhesive solution [solvent: toluene/ethyl acetate=3/1 (weight ratio); concentration: 30 wt. %] with 0.04 parts of TETRAD-X (product of Mitsubishi Gas Chemical Company, Inc.) added to 100 parts (solid content) of the copolymer (Pressure Sensitive Adhesive ⑤). A pressure sensitive adhesive tape for skin was produced in the same manner as in Example 5 except that this pressure sensitive adhesive solution was used.

Comparative Example 8

An acrylic copolymer obtained by copolymerizing isononyl acrylate/methoxyethylene glycol acrylate/acrylic acid (68 parts/30 parts/2 parts) was used as a pressure sensitive adhesive to prepare a pressure sensitive adhesive solution [solvent: toluene/ethyl acetate=3/1 (weight ratio); concentration: 30 wt. %] with 0.04 parts of TETRAD-X (product of Mitsubishi Gas Chemical Company, Inc.) added to 100 parts (solid content) of the copolymer (Pressure Sensitive Adhesive ⑥). A pressure sensitive adhesive tape for skin was produced in the same manner as in Example 5 except that this pressure sensitive adhesive solution was used.

The physical properties of the respective base materials used in Examples 3 to 8, and Comparative Examples 4 to 8, the characteristics of the resultant respective pressure sensitive adhesive tapes, and the results of performance evaluation thereof are shown in Tables 4, 5 and 6, respectively.

TABLE 4

| | Base material | | | | | | |
|---|---|---|---|---|---|---|---|
| | Thickness (μm) | Stress at 15% elongation (N/15 mm) | | Average pore size (μm) | Air permeability (sec/100 cc) | Water-vapor transmission rate (g/m² · 24 h) | Kind |
| | | MD | TD | | | | |
| Ex. 3 | 53 | 5.3 | 4.3 | 1.0 | 160 | 5000 | A |
| Ex. 4 | 50 | 4.4 | 1.0 | 0.9 | 110 | 5500 | B |
| Ex. 5 | 82 | 7.8 | 2.1 | 1.4 | 220 | 4270 | C |
| Ex. 6 | 53 | 5.3 | 4.3 | 1.0 | 160 | 5000 | A |
| Ex. 7 | 53 | 5.3 | 4.3 | 1.0 | 160 | 5000 | A |
| Ex. 8 | 53 | 5.3 | 4.3 | 1.0 | 160 | 5000 | A |
| Comp. Ex. 4 | 70 | 6.9 | 6.0 | 1.1 | 850 | 4500 | a |
| Comp. Ex. 5 | 70 | 6.8 | 5.9 | 1.0 | 500 | 5000 | b |
| Comp. Ex. 6 | 100 | 20.0 | 5.7 | 6.7 | 30 | 5100 | c |
| Comp. Ex. 7 | 82 | 7.8 | 2.1 | 1.4 | 220 | 4270 | C |
| Comp. Ex. 8 | 82 | 7.8 | 2.1 | 1.4 | 220 | 4270 | C |

TABLE 5

| | Characteristics of pressure sensitive adhesive tape | | | | | |
|---|---|---|---|---|---|---|
| | Conformability to stretchable film (*1) | | Water-vapor transmission rate (g/m² · 24 h) | Adhesive strength to bakelite (N/15 mm) | Shear deformation of adhesive (mm/12 × 20 mm² · 2N · 30 min) | Kind of pressure sensitive adhesive |
| | N/15 mm | Quotient | | | | |
| Ex. 3 | 2.97 | 3.53 | 1000 | 1.0 | 0.30 | ① |
| Ex. 4 | 2.91 | 3.46 | 1110 | 1.1 | 0.30 | ① |
| Ex. 5 | 3.21 | 3.82 | 900 | 1.0 | 0.30 | ① |
| Ex. 6 | 3.01 | 3.58 | 870 | 1.4 | 0.20 | ② |
| Ex. 7 | 2.99 | 3.55 | 860 | 1.2 | 0.20 | ③ |
| Ex. 8 | 2.88 | 3.42 | 1030 | 1.0 | 0.20 | ④ |
| Comp. Ex. 4 | 3.22 | 3.83 | 110 | 1.0 | 0.30 | ④ |
| Comp. Ex. 5 | 3.21 | 3.82 | 290 | 1.1 | 0.30 | ④ |
| Comp. Ex. 6 | 4.63 | 5.51 | 1210 | 1.2 | 0.30 | ④ |
| Comp. Ex. 7 | 3.94 | 4.69 | 500 | 3.4 | 0.10 | ⑤ |
| Comp. Ex. 8 | 3.96 | 4.71 | 1500 | 4.3 | 0.10 | ⑥ |

(Note)
(*1): The stress at 15% elongation of the stretchable film is 0.84 N/15 mm. The quotient is a value obtained by dividing the conformability (value of stress) of each pressure sensitive adhesive tape to the stretchable film by the stress at 15% elongation of the stretchable film.

TABLE 6

Performance evaluation of pressure sensitive adhesive tape

| | Conformability to skin (*2) (N/15 mm) | Retention of moisture (μS) | Adhesive strength (N/15 mm) After 1 hr. | Adhesive strength (N/15 mm) After 24 hr. | Pain upon peeling | Skin irritation index |
|---|---|---|---|---|---|---|
| Ex. 3 | 0.67 | 90 | 0.8 | 0.6 | 0.3 | 20 |
| Ex. 4 | 0.65 | 80 | 0.8 | 0.6 | 0.3 | 20 |
| Ex. 5 | 0.69 | 110 | 0.8 | 0.6 | 0.3 | 20 |
| Ex. 6 | 0.69 | 90 | 0.9 | 0.6 | 0.4 | 20 |
| Ex. 7 | 0.68 | 100 | 0.9 | 0.6 | 0.4 | 20 |
| Ex. 8 | 0.65 | 90 | 0.8 | 0.6 | 0.3 | 20 |
| Comp. Ex. 4 | 0.70 | 190 | 0.6 | 0.4 | 0.3 | 30 |
| Comp. Ex. 5 | 0.70 | 160 | 0.7 | 0.5 | 0.3 | 30 |
| Comp. Ex. 6 | 0.82 | 70 | 0.9 | 0.7 | 0.3 | 30 |
| Comp. Ex. 7 | 0.81 | 140 | 1.5 | 0.7 | 0.5 | 40 |
| Comp. Ex. 8 | 0.83 | 70 | 1.6 | 1.4 | 0.5 | 40 |

(Note)
(*2): The stress (skin viscoelasticity) of the skin at 15% elongation is 0.31 N/15 mm.

INDUSTRIAL APPLICABILITY

According to the present invention, there can be provided pressure sensitive adhesive tapes for skin, which have stable tackiness upon sweating or during sticking for a long period of time and scarcely causes pain, corneum separation and skin irritation upon its peeling. In the pressure sensitive adhesive tapes for skin according to the present invention, the conformability to skin, moisture permeability and tackiness to skin are all within respective moderate ranges, these characteristics are balanced with one another at a high level, the tackiness upon sweating or during sticking for a long period of time is made stable, and moreover the pain, corneum separation and skin irritation upon its peeling are lightened to a great extent. According to the present invention, there are further provided base materials suitable for use in the pressure sensitive adhesive tapes for skin having such excellent various characteristics. The pressure sensitive adhesive tapes for skin according to the present invention are suitable for uses such as protection of the affected skin parts and operated sites, and percutaneous absorption of drugs.

What is claimed is:

1. A pressure sensitive adhesive tape for skin, comprising a stretchable base material having good moisture permeability and a pressure sensitive adhesive layer formed on at least one side of the base material, wherein the adhesive tape has the following characteristics:
   (a) the conformability to a stretchable film being at most 4.2 times as much as the stress of the stretchable film at 15% elongation;
   (b) the water-vapor transmission rate being at least 500 g/m²·24 h; and
   (c) the adhesive strength to bakelite being at most 1.5 N/15 mm.
2. The pressure sensitive adhesive tape for skin according to claim 1, which has the following characteristics:
   (a) the conformability to a stretchable film being 2.4 to 4.2 times as much as the stress of the stretchable film at 15% elongation;
   (b) the water-vapor transmission rate being 700 to 5,000 g/m²·24 h; and
   (c) the adhesive strength to bakelite being 0.6 to 1.5 N/15 mm.
3. The pressure sensitive adhesive tape for skin according to claim 1, wherein (d) the shear deformation (mm/12×20 mm²·2 N·30 min) of the pressure sensitive adhesive is 0.15 to 1.20 mm.
4. The pressure sensitive adhesive tape for skin according to claim 1, wherein the stretchable base material having good moisture permeability is a microporous film formed from a resin composition comprising a polyolefin resin and an inorganic filler, and having the following characteristics:
   (1) the thickness being 40 to 200 μm;
   (2) the average pore size being 0.02 to 10 μm;
   (3) the air permeability being 10 to 400 sec/100 cc;
   (4) the water-vapor transmission rate being 1,000 to 20,000 g/m²·24 h; and
   (5) the stresses at 15% elongation in the machine direction and transverse direction being both 0.5 to 15 N/15 mm.
5. The pressure sensitive adhesive for skin according to claim 1, wherein the pressure sensitive adhesive layer is a layer of an acrylic pressure sensitive adhesive.
6. The pressure sensitive adhesive for skin according to claim 5, wherein the acrylic pressure sensitive adhesive is a copolymer comprising:
   (i) 50 to 97.5 wt. % of an alkyl (meth)acrylate having an alkyl group having 4 to 12 carbon atoms;
   (ii) 2 to 49.5 wt. % of an alkoxypolyalkylene glycol (meth)acrylate; and
   (iii) 0.5 to 15 wt. % of a hydroxyl group- or carboxyl group-containing monomer.
7. The pressure sensitive adhesive for skin according to claim 6, wherein the alkoxypolyalkylene glycol (meth)acrylate is a (meth)acrylic ester represented by the formula (1):

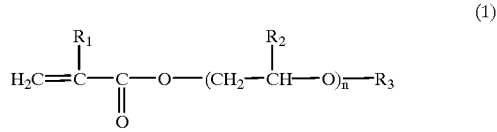

(1)

wherein $R_1$ and $R_2$ are independently a hydrogen atom or a methyl group, $R_3$ is an alkyl group having 1 to 20 carbon atoms, and n is an integer of 2 to 12.
8. The pressure sensitive adhesive for skin according to claim 6, wherein the hydroxyl group-containing monomer is a hydroxyalkyl (meth)acrylate.
9. The pressure sensitive adhesive for skin according to claim 6, wherein the carboxyl group-containing monomer is a carboxyalkyl (meth)acrylate.
10. The pressure sensitive adhesive for skin according to claim 6, wherein the hydroxyl group-containing monomer is a hydroxyl group-containing (meth)acrylic ester represented by the formula (2):

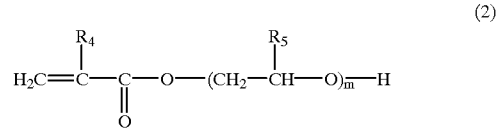

(2)

wherein $R_4$ and $R_5$ are independently a hydrogen atom or a methyl group, and m is an integer of 2 to 12.
11. The pressure sensitive adhesive for skin according to claim 6, wherein the carboxyl group-containing monomer is a carboxyl group-containing (meth)acrylic ester represented by the formula (3):

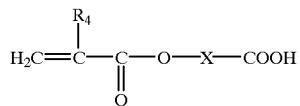
(3)

wherein $R_6$ is a hydrogen atom or a methyl group, and X is a divalent organic group having at least 2 carbon atoms and may contain a heteroatom such as an oxygen, nitrogen or sulfur atom.

12. A base material of a pressure sensitive adhesive tape for skin, comprising a microporous film formed from a resin composition comprising a polyolefin resin and an inorganic filler, and having the following characteristics:
   (1) the thickness being 40 to 200 μm;
   (2) the average pore size being 0.02 to 10 μm;
   (3) the air permeability being 10 to 400 sec/100 cc;
   (4) the water-vapor transmission rate being 1,000 to 20,000 g/m²·24 h; and
   (5) the stresses at 15% elongation in the machine direction and transverse direction being both 0.5 to 15 N/15 mm.

13. The pressure sensitive adhesive tape for skin according to claim 2, wherein (d) the shear deformation (mm/12× 20 mm²·2 N·30 min) of the pressure sensitive adhesive is 0.15 to 1.20 mm.

14. The pressure sensitive adhesive tape for skin according to claim 2, wherein the stretchable base material having good moisture permeability is a microporus film formed from a resin composition comprising a polyolefin resin and an inorganic filler, and having the following characteristics:
   (1) the thickness being 40 to 200 μm;
   (2) the average pore size being 0.02 to 10 μm;
   (3) the air permeability being 10 to 400 sec/100 cc;
   (4) the water-vapor transmission rate being 1,000 to 20,000 g/m²·24 h; and
   (5) the stresses at 15% elongation in the machine direction and transverse direction being both 0.5 to 15 N/15 mm.

15. The pressure sensitive adhesive for skin according to claim 2, wherein the pressure sensitive adhesive layer is a layer of an acrylic pressure sensitive adhesive.

* * * * *

UNITED STATES PATENT AND TRADEMARK OFFICE
CERTIFICATE OF CORRECTION

PATENT NO. : 6,262,330 B1
DATED : July 17, 2001
INVENTOR(S) : Hiromichi Fujisawa et al.

It is certified that error appears in the above-identified patent and that said Letters Patent is hereby corrected as shown below:

Column 23,
Lines 3-8, delete formula (3) in its entirety and insert the following therefore:

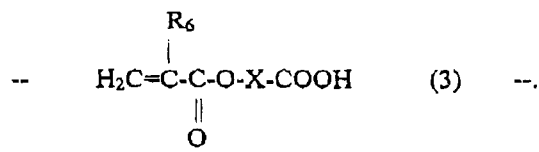

Signed and Sealed this

Seventeenth Day of September, 2002

Attest:

Attesting Officer

JAMES E. ROGAN
Director of the United States Patent and Trademark Office